US008469707B2

(12) United States Patent
Emde

(10) Patent No.: US 8,469,707 B2
(45) Date of Patent: Jun. 25, 2013

(54) HAND-HELD DEVICE FOR DISPENSING A PASTY FILLING MATERIAL

(75) Inventor: Frank Emde, Memmingen (DE)

(73) Assignee: Kaltenbach & Voigt GmbH, Biberach (DE)

( * ) Notice: Subject to any disclaimer, the term of this patent is extended or adjusted under 35 U.S.C. 154(b) by 455 days.

(21) Appl. No.: 12/599,767

(22) PCT Filed: May 8, 2008

(86) PCT No.: PCT/EP2008/003705
§ 371 (c)(1),
(2), (4) Date: Feb. 17, 2010

(87) PCT Pub. No.: WO2008/138545
PCT Pub. Date: Nov. 20, 2008

(65) Prior Publication Data
US 2010/0304322 A1  Dec. 2, 2010

(30) Foreign Application Priority Data
May 11, 2007  (DE) .......................... 10 2007 022 205

(51) Int. Cl.
*A61C 3/08*  (2006.01)
*A61C 5/04*  (2006.01)
*A61C 1/07*  (2006.01)

(52) U.S. Cl.
USPC .................. 433/29; 433/80; 433/83; 433/89; 433/31; 433/86; 601/17; 362/573; 362/804

(58) Field of Classification Search
USPC ................. 433/29–31, 36, 80, 82, 83, 86, 88, 433/89, 121, 164, 27, 28, 32; 604/29; 606/13; 362/573, 804; 250/504 R, 492.1, 492.3, 493.1; 222/196, 409, 144.5, 145.1; 601/15–18, 72, 601/73, 80
See application file for complete search history.

(56) References Cited

U.S. PATENT DOCUMENTS

| 3,221,409 | A | * | 12/1965 | Thiel et al. ..................... 433/83 |
| 3,487,828 | A | * | 1/1970 | Troy ............................. 601/162 |
| 3,552,021 | A | * | 1/1971 | Graceffo et al. ............. 433/121 |
| 3,667,454 | A | * | 6/1972 | Prince ............................ 601/18 |
| 3,850,346 | A | * | 11/1974 | Richardson et al. ....... 222/145.7 |
| 4,076,148 | A | * | 2/1978 | Carse ......................... 222/144.5 |
| 4,092,778 | A | * | 6/1978 | Hirdes ............................ 433/83 |
| 4,291,685 | A | * | 9/1981 | Taelman ......................... 601/17 |
| 4,673,353 | A | | 6/1987 | Nevin |
| 4,768,955 | A | * | 9/1988 | Hirdes ............................ 433/89 |
| 4,850,875 | A | * | 7/1989 | Takatsu ......................... 433/226 |
| 5,003,434 | A | * | 3/1991 | Gonser et al. ................. 362/572 |
| 5,007,837 | A | | 4/1991 | Werly |
| 5,415,543 | A | * | 5/1995 | Rozmajzl, Jr. .................. 433/29 |

(Continued)

FOREIGN PATENT DOCUMENTS
CA  2190225 A1  6/1997
CA  2190226 A1  6/1997

(Continued)

*Primary Examiner* — Robyn Doan
*Assistant Examiner* — Tatiana Nobrega
(74) *Attorney, Agent, or Firm* — Marshall, Gerstein & Borun LLP

(57) ABSTRACT

A hand-held device, particularly for dental purposes, comprising a dispenser for dispensing a pasty filling material as well a device for emitting a radiation that causes the filling material to cure.

10 Claims, 3 Drawing Sheets

U.S. PATENT DOCUMENTS

| | | | | |
|---|---|---|---|---|
| 5,547,374 A | * | 8/1996 | Coleman | 433/85 |
| 5,697,784 A | * | 12/1997 | Hafele et al. | 433/85 |
| 5,908,295 A | * | 6/1999 | Kawata | 433/29 |
| 5,961,235 A | * | 10/1999 | Kennedy | 401/6 |
| 6,200,134 B1 | * | 3/2001 | Kovac et al. | 433/29 |
| 6,305,934 B1 | * | 10/2001 | Hatley, Jr. | 433/80 |
| 6,312,254 B1 | * | 11/2001 | Friedman | 433/32 |
| 6,386,866 B1 | * | 5/2002 | Hecht et al. | 433/29 |
| 6,494,714 B1 | * | 12/2002 | Copeland | 433/86 |
| 6,510,966 B1 | * | 1/2003 | Perry et al. | 222/145.6 |
| 6,616,448 B2 | * | 9/2003 | Friedman | 433/32 |
| 6,769,573 B1 | * | 8/2004 | Kazarian et al. | 222/136 |
| 7,086,861 B2 | * | 8/2006 | Pitz et al. | 433/90 |
| 7,090,097 B1 | * | 8/2006 | Kazarian et al. | 222/144.5 |
| 7,270,439 B2 | * | 9/2007 | Horrell et al. | 362/119 |
| 7,273,369 B2 | * | 9/2007 | Rosenblood et al. | 433/29 |
| 7,487,889 B2 | * | 2/2009 | Owens | 222/144.5 |
| 7,533,786 B2 | * | 5/2009 | Woolfson et al. | 222/144.5 |
| 7,938,296 B2 | * | 5/2011 | Keller | 222/145.5 |
| 2003/0194678 A1 | * | 10/2003 | Viltro et al. | 433/80 |
| 2004/0131992 A1 | * | 7/2004 | Lashmore | 433/83 |
| 2004/0164670 A1 | * | 8/2004 | Nanni et al. | 313/503 |
| 2005/0130099 A1 | * | 6/2005 | Besek et al. | 433/80 |
| 2005/0202364 A1 | * | 9/2005 | Fornasari et al. | 433/88 |
| 2006/0183071 A1 | * | 8/2006 | Hsuch | 433/29 |
| 2006/0234185 A1 | * | 10/2006 | Ziemba | 433/119 |
| 2007/0080170 A1 | * | 4/2007 | Saha | 222/142.1 |
| 2007/0105064 A1 | * | 5/2007 | Lynch et al. | 433/80 |
| 2008/0096157 A1 | * | 4/2008 | Ziemba | 433/29 |
| 2008/0206706 A1 | * | 8/2008 | Mossle | 433/118 |
| 2008/0213731 A1 | * | 9/2008 | Fishburne | 433/217.1 |
| 2009/0047619 A1 | * | 2/2009 | Oh et al. | 433/32 |
| 2009/0097270 A1 | * | 4/2009 | Becker et al. | 362/573 |

FOREIGN PATENT DOCUMENTS

| | | |
|---|---|---|
| DE | 29517958 | 3/1997 |
| DE | 19619154 A1 | 6/1997 |
| DE | 19619155 A1 | 6/1997 |
| DE | 10001513 A1 | 4/2001 |
| WO | WO 2005120382 A1 * | 12/2005 |
| WO | WO-2006/136398 A2 | 12/2006 |

* cited by examiner

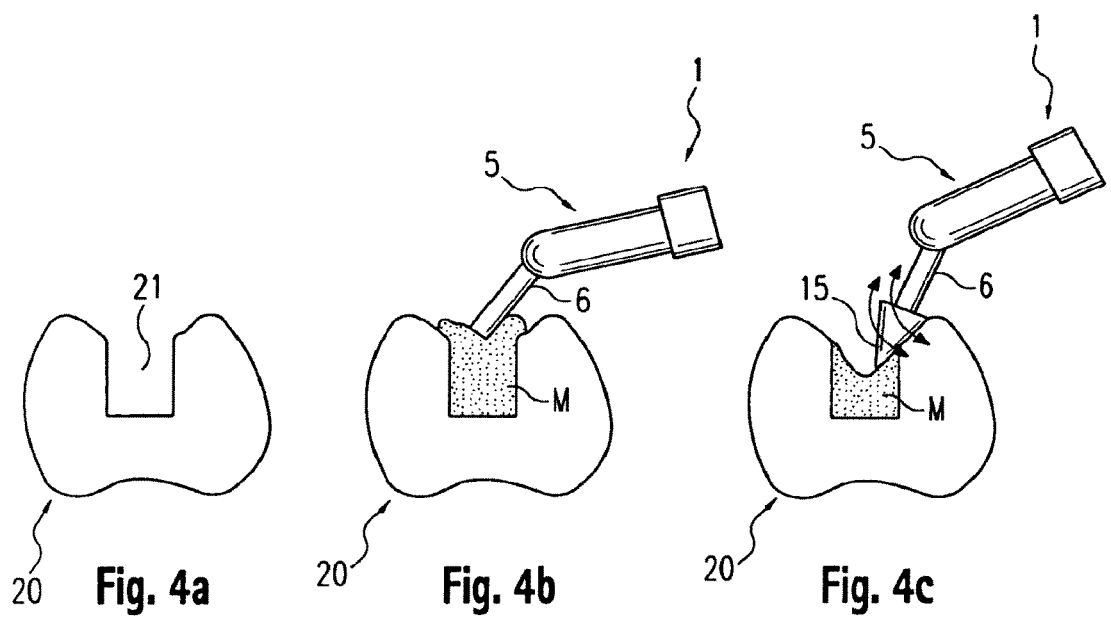

HAND-HELD DEVICE FOR DISPENSING A PASTY FILLING MATERIAL

BACKGROUND OF THE INVENTION

1. Field of the Invention

The invention relates to a hand-held device that is provided in particular for dental purposes and comprises means for dispensing a pasty filling material.

2. Related Technology

In medical technology, it is known to fill cavities in an animal or human body part with a filling material capable of hardening. For this purpose, filling materials are used which are introduced into the cavity in a pasty or liquid state and subsequently harden or are hardened. Hardening of these filling materials can be assisted in particular by irradiation thereof with light of a suitable wavelength.

A dental hand-held device which is configured for dispensing a pasty filling compound is known from WO 2006/136398 A2. In this case, it is proposed inter alia to subject the filling compound to ultrasound during dispensing, as a result of which the filling compound can be introduced more effectively into the cavity.

Typically, the process of introducing the light-hardening filling materials is performed in layers, in order to fill the cavity in an optimum fashion. In this case, a small amount of the filling material is introduced in each case into the cavity and is subsequently hardened which can be performed e.g. with the aid of a light polymerization lamp, as described in the publications DE 196 19 154 A1 and DE 196 19 155 A1. In turn, filling material is then introduced in a further operating step into the cavity and is hardened, wherein this alternating procedure is repeated until the cavity has been completely filled.

SUMMARY OF THE INVENTION

The invention provides an improved hand-held device, of the type known e.g. from WO 2006/136398 A2, such that the operating procedures are facilitated for a user, in particular a dentist.

Accordingly, the invention provides hand-held device, in particular for dental purposes, having means for dispensing a pasty filling material, and means located on the hand-held device for emitting radiation that effects hardening of the filling material.

In accordance with the present invention, a hand-held device, in particular for dental purposes, is proposed which initially comprises means for dispensing a pasty filling material. In accordance with the invention, the hand-held device is characterized by virtue of the fact that in addition means are provided on the hand-held device for emitting a radiation which effects hardening of the filling material.

The solution in accordance with the invention is thus based upon the idea that a hand-held device is now provided which fulfils both purposes—dispensing the pasty filling material and radiation-induced hardening of the filling material. As a consequence, when introducing the filling into the tooth cavity a dentist does not have to continuously alternate between two different devices but instead can use a single device throughout the entire operating procedure. This not only serves to facilitate the implementation of the procedure but also serves to save a considerable amount of time. Furthermore, the quality of the operating procedure can be improved, as it is no longer necessary to reapply a hand-held device repeatedly to the tooth which is to be treated.

The means for emitting radiation are preferably formed by a light source. Furthermore, the means for dispensing the filling material can include an outlet nozzle which is located on a front end of the hand-held device. In the case of a particularly preferred exemplified embodiment of the present invention, this can be part of a compacting element which can be subjected to ultrasonic oscillations via a drive unit located in the hand-held device. The purpose of using the ultrasonic oscillations can be not only to increase the viscosity of the filling material as it is dispensed, as described in WO 2006/136398 A2, but also the compound introduced into the cavity can initially be compacted with the aid of the compacting element, before the compound is hardened in a manner induced by light.

It can also be provided that after the filling material is dispensed the outlet nozzle is provided with a modeling tip which is used in order to model the material to the desired shape, in particular to remove any excess material, before final hardening of the material. It has been shown that in the case where this tip is subjected to sound or ultrasound, particularly simple but precise working of the material is rendered possible, so that ultimately very high quality fillings can be produced.

The outlet nozzle is preferably formed in such a manner that the filling material is dispensed laterally with respect to a longitudinal axis of the hand-held device. In this case, it is also provided that the means for emitting radiation are formed in such a manner that with regard to the longitudinal axis of the hand-held device the emission of the radiation is effected in an offset manner, preferably offset by 90° in comparison with the dispensing of the filling material. When a change is made between dispensing the filling material and hardening with the aid of the light, the hand-held device must only be rotated by 90°, which simplifies handling notably. Furthermore, by reason of this specific configuration it is ensured that the filling material is not already hardened inadvertently as it is being dispensed.

Other developments of the invention relate to ideas which once again serve to further improve the implementation of treatment. Therefore, it can be provided e.g. that means are provided on the hand-held device for selecting and changing the viscosity of the dispensed filling material. In this case, the viscosity of the material can be adjusted as it is being dispensed which can yield particular advantages depending upon the nature of the cavity. In particular, it is ensured that the cavity can be filled by the material without any gaps.

A further possibility resides in the fact that filling materials having different properties, in particular different colors, are provided in the hand-held device. With the aid of a corresponding selection mechanism, a material having the desired property can then be dispensed, so that depending upon requirement an implementation [sic] of the cavity can be performed in the desired manner.

As already mentioned above, it can be provided in particular that the filling material is subjected to ultrasound as it is being dispensed. However, it would also be feasible to dispense the filling material with the aid of a mechanical plunger.

BRIEF DESCRIPTION OF THE DRAWINGS

The invention will be described in more detail hereinafter with reference to the accompanying drawing, in which

FIGS. 4a to 4c show the mode of operation with a further modified form of the hand held device.

DETAILED DESCRIPTION

Figure 1:
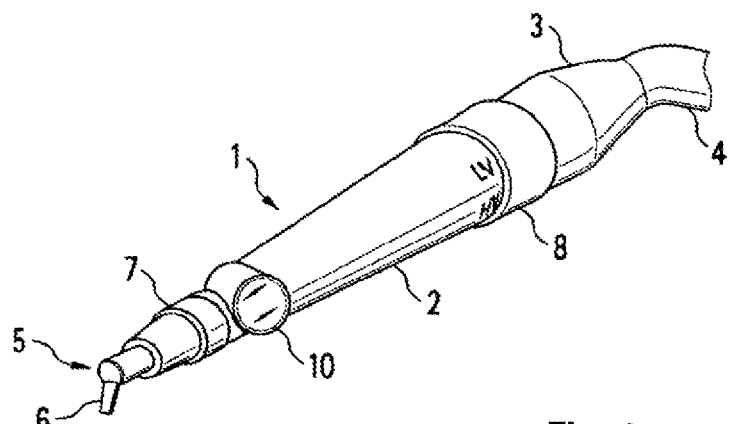
FIG. 1 shows an exemplified embodiment of a hand-held device in accordance with the invention in a perspective illustration.

The hand-held device in accordance with the invention which is illustrated in FIG. 1 and designated generally by the reference numeral 1 has an elongate handle sleeve 2, on whose rear end coupling elements 3 are provided for connecting to a supply tube 4. The supply tube 4 leads to a supply unit—not illustrated in detail—via which supply media, in particular current, can be provided to the device 1.

In the first instance, the primary objective of the hand-held device 1 is to dispense or provide a pasty filling material, with the aid of which cavities, in particular in teeth, can be filled. For this purpose, an application element 5 is formed on the front end of the hand-held device 1 and comprises an outlet nozzle 6 which protrudes laterally with respect to the longitudinal axis of the handle sleeve 2. The pasty filling material is dispensed as required via this nozzle 6.

As already known from the previously discussed WO 2006/136398 A2, it can be provided that dispensing of the pasty filling material is assisted by ultrasound. Consequently, as the material is being dispensed it is converted into a viscous state by virtue of the fact that the outlet nozzle 6 is subjected to ultrasound accordingly, the viscous state rendering it possible to introduce the filling material in a particularly effective and precise manner. For this purpose, at least one storage container containing the filling material and a corresponding dispensing mechanism are provided inside the device 1 accordingly. Furthermore, an oscillation generator to produce ultrasonic oscillations is also provided in this case. In turn, with regard to the various ways of dispensing the filling material, reference is made to the previously discussed international laid-open document.

As can also be seen from the illustration in FIG. 1, two adjusting rings are provided on the hand-held device 1. In this case, a first adjusting ring 7 disposed in the front region serves to selectively open and close a dispensing channel leading from the storage container for the filling material to the outlet nozzle 6, in order to prevent any corresponding material from issuing out undesirably. However, with the aid of the second rear adjusting ring 8, the viscosity of the dispensed material can be adjusted between at least two different regions. An optional change in the viscosity which can be performed e.g. by controlling the oscillation generator accordingly, offers advantages insofar as the viscosity can be adapted to suit the corresponding shape of the cavity to be filled. Particularly in the case of cavities having regions which are difficult to reach it is practical to introduce a material with a relatively high viscosity, as in this case the cavity can be filled more effectively.

However, as an alternative to the use of an ultrasonic generator as the filling material is being dispensed, it can also be provided that the filling material is dispensed mechanically by a plunger without the application of sound.

Another feasible development would be to use several storage containers containing filling materials having different properties, e.g. different colors. Depending upon requirement, it is possible by correspondingly adjusting the selection ring 8 to select a suitable storage container, whose material can then be introduced via the outlet nozzle 6 into the cavity with the aid of a suitable dispensing mechanism. As a consequence, it is possible to introduce at any time a material which in terms of its external configuration adapts in an optimum manner to the tooth which is to be treated. This idea of selecting from different filling materials, which can be implemented e.g. in the form of a revolver mechanism, could also be utilized in particular independently of the idea of supplementing the device 1 with irradiation means as described hereinafter.

The hand-held device 1 described up to this point thus serves on the one hand to provide filling materials which can be used for filling a tooth cavity. As already mentioned in the introduction, such materials often have the property that they can be hardened more effectively by means of suitable irradiation. In order to avoid having to alternate continuously between different devices during treatment, the hand-held device 1 is equipped in accordance with the invention with irradiation means which are to be explained hereinafter.

The irradiation means merely schematically indicated in FIG. 1 are formed by means of a light source 10, via which light of a suitable wavelength (e.g. in the range of about 320 nm to 550 nm) is emitted. This light effects hardening of the filling material, as already known from the publications DE 196 19 154 A1 and DE 196 19 155 A1. As can also be seen from the illustration, the light source 10 which could be formed e.g. by an LED or a laser diode is disposed in the front region of the handle sleeve 2, but in such a manner that with regard to the longitudinal axis of the device 1 the light is emitted in a skewed manner, preferably skewed by 90°, with respect to the orientation of the outlet nozzle 6. As a consequence, it is ensured that as the filling material is being dispensed from the outlet nozzle 6 the filling material can in no way be irradiated by the light source 10 and accordingly it is not able to harden prematurely. It is thus ensured that as previously the material can be dispensed effectively in the usual manner.

The mode of operation applied in the case of the hand-held device 1 in accordance with the invention and the advantages achieved in this case will be described hereinafter with reference to FIGS. 2a and 2b and 3a to 3c respectively.

Figure 2A:
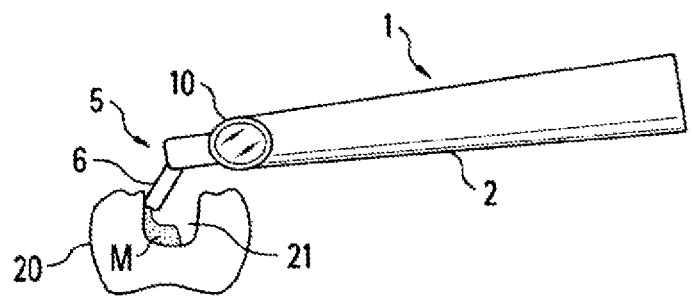
FIGS. 2a and 2b show the operating steps required for filling a tooth cavity using the hand-held device in accordance with the invention.
Figure 2B:
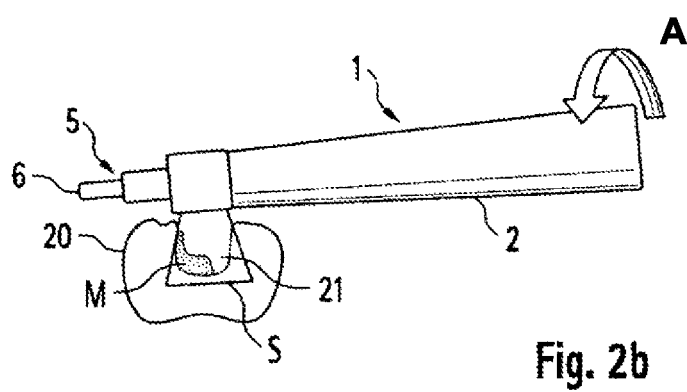

FIGS. 2a and 2b illustrate the various operating steps when using the hand-held device illustrated in FIG. 1. In this case, the cavity 21 of a tooth 20 is to be filled, wherein—as already mentioned—filling material M is introduced in layers into the cavity 21 and the filling material is subsequently hardened. FIG. 2a illustrates in this case the step of introducing the filling material M, which as previously explained is performed via the outlet nozzle 6. In this case, it can be seen from the illustration in FIG. 2a that the light source 10 is aligned or oriented with regard to the nozzle 6 such that it does not illuminate the cavity 21. In other words, the light emitted by the light source 10 does not impair effective filling of the cavity 21.

After a certain amount of filling material M has been introduced, it must initially be hardened before further material is introduced. For this purpose, the dentist must turn the hand-held device 1 through about 90° as illustrated by an arrow A in FIG. 2b, as a result of which the light source 10 is then aligned with the cavity 21 of the tooth 20 and the radiation S for hardening the filling material M can be utilized accordingly. After hardening of the material M is completed, the hand-held device 1 is then turned to the position illustrated in FIG. 2a and material M can be introduced from the beginning.

It is apparent from the depictions above that—without having to change the device—material can be introduced into the cavity and hardened in an alternating manner without encountering any problems. This procedure is correspondingly associated with a relatively substantial time saving. Furthermore, the hand piece does not have to be applied to the tooth each time from the beginning, which simplifies handling considerably.

Figure 3A:
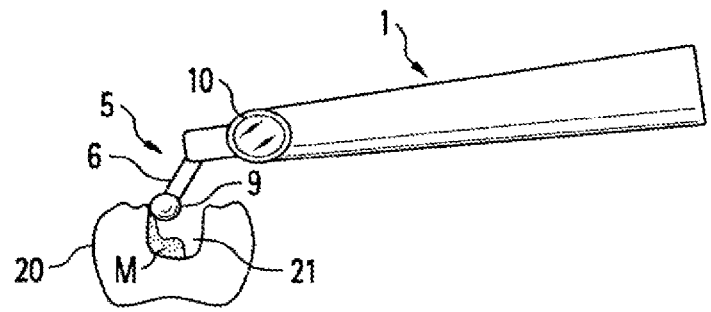
FIGS. 3a to 3c show the mode of operation with an alternative form of the hand-held device, in which compacting of the introduced filling material is provided as an intermediate step.
Figure 3B:
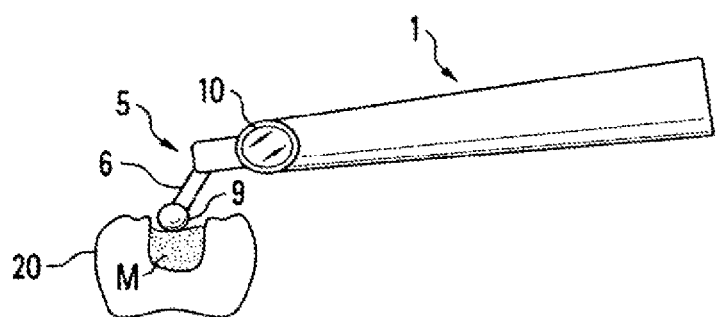
Figure 3C:
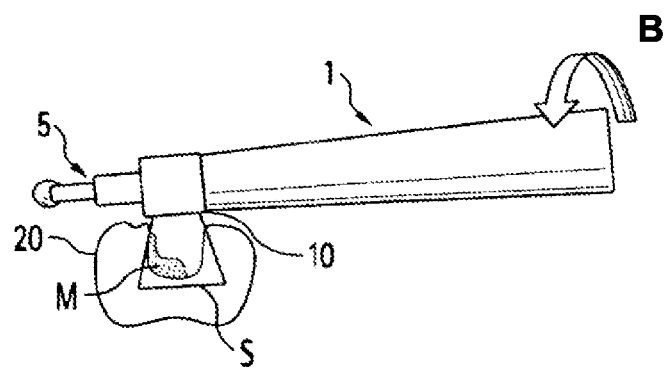

FIGS. 3a to 3c illustrate the use of an alternative exemplified embodiment of a hand-held device 1 in accordance with the invention. It is characterized by virtue of the fact that a compacting element 9 in the form of a spherical attachment is disposed in addition at the front end of the outlet nozzle 6. In the same manner as the nozzle 6, this attachment 9 is subjected to ultrasonic oscillations by means of a generator located in the hand-held device 1.

After filling material M has been introduced into the cavity 21 in a manner corresponding to the illustration in FIG. 3a, the filling material is initially compacted with the aid of the compacting element 9 which is caused to produce ultrasonic oscillations. In this case, the properties of the filling material M change in a positive manner. Subsequently, the introduced and compacted filling compound M is illuminated and hardened in turn upon rotation of the hand-held device 1, as illustrated by an arrow B in FIG. 3c. The illustrated operating steps are repeated in turn several times until the cavity 21 of the tooth 20 has been completely filled.

In the case of this alternative embodiment, it is not necessary to alternate between several different devices, which in turn results in a very convenient implementation of the procedure.

A third variant of a hand-held device 1 in accordance with the invention is illustrated in FIGS. 4a to 4c, wherein in this case only the front end region of the hand-held device 1 is illustrated. In turn, the cavity 21 of a tooth 20 is initially filled with the filling material M, wherein the filling material M is dispensed in the same manner as previously via the outlet nozzle 6 of the application element 5 and the nozzle 6 is subjected to ultrasound as the material M is being dispensed.

In a further operating step which is illustrated in FIG. 4c, the filling material M is modeled into the ultimately required form. For this purpose, the front end of the outlet nozzle 6 is provided with a—preferably conically formed—modeling tip 15, with the aid of which the material is worked. The nozzle 6 and thus also the modeling tip 15 are in turn subjected to ultrasound during this working procedure.

This particular procedure is based upon the knowledge that by reason of the partially very limited thermal development and the breakup of chemical compounds by sound or ultrasonic sources, composites of this type can be very easily carved and/or shaped. This effect is utilized in filling therapy in order to convert the highly viscous filling materials into the desired anatomical tooth form.

The proposed method represents considerable progress in comparison with the previous procedure. In the case of previous methods, it is necessary to distribute excess filling material over the preparation edges—in particular in the occlusal region—using a spatula and to let it run out in a thin film on the occlusal surface or ideally to completely remove it. Since it is not always entirely possible to achieve this or since the surface continuity of the material is damaged during removal, it is necessary after hardening of the material to remove it with an abrasive wheel. This is time-consuming and healthy tooth substance is frequently also removed. Furthermore, modeling is difficult to perform, as the corresponding anatomical tooth form can only be restored with difficulty merely by "pressing" the filling compound.

However, in the case of the method proposed in FIGS. 4a to 4c the excess filling material is simply "melted off" so to speak with the aid of the modeling tip 15. Should the occlusal surface of the tooth 20 still be present for the main part, then it can be used as a support and "guiding path" in order to produce an anatomically correct configuration. This also offers a time advantage as where there are fewer or no residues the occlusal surface subsequently has to be ground to a lesser extent or not at all and the shaping procedure is completed much more quickly. In the event of restoration of front teeth, shaping can also be effected very easily because in this case it is also possible to make a very smooth transition from healthy tooth substance to tooth substance to be replaced— even during modeling in the plastic state. In the case of previous methods, very extensive grinding generally has to be carried out after hardening of the material.

In the illustrated example, the modeling tip 15 fulfils a dual function as it can also be used at the same time as a closure cap for the composite cartridges. In this case, the sonic or ultrasonic waves are transmitted via the cartridge to the closure cap.

After the filling material M has been worked, it is then hardened, for which reason it is possible in turn to use the light source which is disposed on the hand-held device 1 but is not illustrated in the Figures. However, the idea illustrated in FIGS. 4a to 4c can also be used irrespective of whether the light source is mounted on the hand-held device 1 itself or a separate light source is used for the hardening procedure. Furthermore, the modeling tip 15 could also be used on a working tool which is independent of the hand-held device for dispensing the filling material M and which renders it possible to apply sonic or ultrasonic waves to the tip 15.

On the whole, the implementation of a treatment is correspondingly simplified to a considerable extent for the dentist. Furthermore, by reason of the different selection options with regard to viscosity or material properties of the filling material it is possible to fill the tooth with a specifically suitable material in each case. In this case, the quality of the treatment is thus significantly improved.

The invention claimed is:
1. Hand-held device comprising:
a dispenser for dispensing a pasty filling material; and
an emitter located on the hand-held device for emitting radiation that effects hardening of the filling material, wherein the dispenser comprises an outlet nozzle located on a front end of the hand-held device,
the outlet nozzle is part of a compacting element that can be subjected to sonic or ultrasonic oscillations via a drive unit located in the hand-held device,
the outlet nozzle is formed in such a manner that the filling material is dispensed laterally with respect to a longitudinal axis of the hand-held device,
the emitter is formed in such a manner that with regard to the longitudinal axis of the hand-held device the emission of the radiation is effected in an offset manner with respect to the dispensing of the filling material, and
the emitter is formed in such a manner that with regard to the longitudinal axis of the hand-held device the emission of the radiation is offset rotationally about the longitudinal axis of the hand-held device by approximately 90° relative to the outlet nozzle.

2. Hand-held device as claimed in claim 1, wherein the emitter comprises a light source.

3. Hand-held device as claimed in claim 2, wherein the light source comprises an LED or laser diode.

4. Hand-held device as claimed in claim 1, comprising a modeling tip, which can be attached to the outlet nozzle, for working the filling material, wherein the modeling tip can be subjected to sonic or ultrasonic oscillations via a drive unit located in the hand-held device.

5. Hand-held device as claimed in claim 4, wherein the modeling tip has a conical shape.

6. Hand-held device as claimed in claim 1, comprising an adjuster for adjusting the viscosity of the dispensed filling material.

7. Hand-held device as claimed in claim 1, comprising means for selectively opening and closing a dispensing channel for the filling material.

8. Hand-held device as claimed in claim 1, comprising a plurality of storage containers for filling materials having different properties and selection means for selectively dispensing one of the filling materials.

9. Hand-held device as claimed in claim 8, wherein the selection means includes a first adjusting ring disposed in a front region of the hand-held device and a second adjusting ring on the hand-held device aft of the first adjusting ring.

10. The hand-held device of claim 9, wherein the first adjusting ring selectively opens and closes a dispensing channel leading from one storage container in the plurality of storage containers to the outlet nozzle and the second adjusting ring controls an oscillation generator connected to the hand-held device to vary viscosity of the pasty filling material.

* * * * *

UNITED STATES PATENT AND TRADEMARK OFFICE
CERTIFICATE OF CORRECTION

PATENT NO.       : 8,469,707 B2
APPLICATION NO. : 12/599767
DATED            : June 25, 2013
INVENTOR(S)      : Frank Emde It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 551 days.

Signed and Sealed this
Eighth Day of September, 2015

Michelle K. Lee
*Director of the United States Patent and Trademark Office*